United States Patent [19]

Arnaud et al.

[11] 4,221,722

[45] Sep. 9, 1980

[54] PROCESS FOR PREPARING ALKYLPYRYLIUM SALTS

[75] Inventors: Michel Arnaud; Christian Roussel, both of Marseilles, France

[73] Assignee: Rhone-Poulenc Industries, Paris, France

[21] Appl. No.: 960,610

[22] Filed: Nov. 14, 1978

[30] Foreign Application Priority Data

Nov. 18, 1977 [FR] France .................. 77 35292

[51] Int. Cl.$^2$ ............... C07D 309/34; C07D 213/18
[52] U.S. Cl. ................... 260/345.1; 546/253; 546/250
[58] Field of Search ...................... 260/345.1

[56] References Cited

U.S. PATENT DOCUMENTS

| T900,031 | 7/1972 | Petropoulos et al. | 260/345.1 |
|---|---|---|---|
| 3,148,067 | 9/1964 | Reynolds | 260/345.1 |
| 3,250,615 | 5/1966 | Van Allen et al. | 260/345.1 |

FOREIGN PATENT DOCUMENTS

| 1340970 | 10/1963 | France . |
|---|---|---|
| 1340971 | 10/1963 | France . |
| 1387433 | 1/1965 | France . |

OTHER PUBLICATIONS

Balaban et al., J.A.C.S., pp. 3553–3561 (1961).
Hopff et al., Ber. 69, 2244–2251 (1936).
Balaban, Advances in Heterocyclic Chem., vol. 10, pp. 214–326 (1969).
Van Allan et al., Chem. Absts., 63, 10102(d), 1965.
Krivun et al., Russ. Chem. Rev., 43, 835–850 (1974).
Balaban et al., Ann., 625, pp. 74–88 (1959).

*Primary Examiner*—G. T. Breitenstein
*Attorney, Agent, or Firm*—Burns, Doane, Swecker & Mathis

[57] ABSTRACT

A process for preparing polyalkylpyrylium salts comprising a polyalkylpyrylium cation, wherein the pyrylium nucleus is substituted by 3 to 5 alkyl substituents three of which are situated in the 2-, 4- and 6-position is disclosed which comprises the step of reacting a branched alkane comprising at least one tertiary carbon atom with an acylating agent which is a reactive alkylcarboxylic acid derivative and an alkyl halide in the presence of a Lewis acid catalyst selected from the group consisting of aluminum halides, ferric halides and mixtures thereof.

19 Claims, No Drawings

PROCESS FOR PREPARING ALKYLPYRYLIUM SALTS

BACKGROUND OF THE INVENTION

The present invention relates to a process for preparing alkylpyrylium salts, containing at least three alkyl groups in the 2-, 4- and 6-position, by reacting a branched alkane with an acylating agent in the presence of a Lewis acid.

The pyrylium salts represented by the general formula:

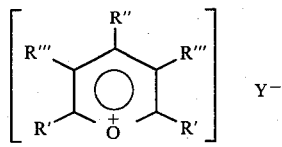

wherein R' and R" each represent alkyl, each R''' represents hydrogen or alkyl, and Y⁻ represents an acid anion, are compounds which are known in the art and are of very great industrial value in various respects. Thus, they are used as adjuvants in photosensitive compositions employed in photography (see, e.g., French Pat. No. 1,387,433 and U.S. Pat. No. 3,250,615). Furthermore, pyrylium salts constitute intermediates which are in great demand in organic synthesis. Thus, reaction of pyrylium salts with ammonia or amines, leads to the corresponding pyridine bases. By the action of an alkali metal base such as sodium hydroxide, trisubstituted pyrylium salts containing a methyl group in the 2-position are converted into disubstituted phenols. Apart from these reactions which are of particular importance from the industrial point of view, pyrylium salts are applied in numerous other ways in organic synthesis (see, e.g., S. V. KRIVUN et al., Russ. Chem. Rev., 43, 835–850 (1974)).

The synthesis of pyrylium salts has been the subject of numerous works (compare A. T. BALABAN, Advances in Heterocyclic Chemistry volume 10, pages 214–326 (1969)). Among the various processes for preparing the above alkylpyrylium salts, the most valuable industrially are those which employ diacylation of olefins or their precursors such as tertiary alkyl halides or tertiary or secondary alcohols or their esters, in the presence of Lewis acids such as the halides of various metals (for example AlCl₃, FeCl₃, SbCl₅, SnCl₄ or ZnCl₂) or boron trifluoride or its complexes with alkyl ethers (ethyl or isopropyl ether) or also in the presence of a strong Bronsted acid such as perchloric acid or trifluoromethanesulphonic acid. Acylating agents used are acid anhydrides and more particularly the halides of aliphatic or aromatic acids. The diacylation of olefins can be presented schematically as follows:

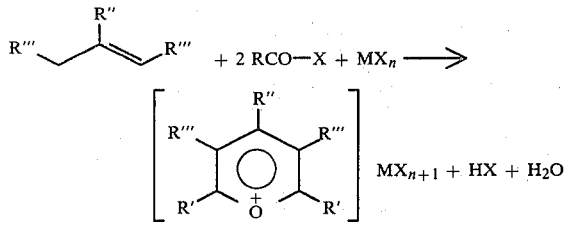

The yields of pyrylium salts vary according to the olefin (or its precursor), the acylating agent and the catalyst used (compare A. T. BALABAN et al., Ann., 625, pages 74 to 88 (1959), J. Chem. Soc., 1961, pages 3,553–3,561 and French Pat. Nos. 1,340,970 and 1,340,971).

Despite the value of the diacylation of olefins it appears to be desirable from the industrial point of view to have available a process for the preparation of pyrylium salts from branched alkanes or their mixtures such as the fractions of saturated aliphatic hydrocarbons which are available on an industrial scale. It is surprising to find that, although the diacylation of olefins or their precursors has formed the subject of numerous works since 1959, there are no publications on the preparation of pyrylium salts from branched alkanes. Indeed, H. HOPFF et al, (Ber., 69, pages 2,244 to 2,251 (1936)) have studied the reaction of acetyl chloride with saturated hydrocarbons, and in particular with isobutane, but they do not observe the formation of pyrylium salts.

SUMMARY OF THE INVENTION

It is an object of the present invention to provide a process for preparing alkyl-substituted pyrylium salts from branched alkanes.

It is a special object of the present invention to provide such a process by means of which alkyl-substituted pyrylium salts can be obtained from branched alkanes or mixtures of branched and unbranched alkanes which are readily available, e.g., a paraffin cut.

In order to accomplish the foregoing objects there is provided a process for preparing polyalkylpyrylium salts comprising a polyalkylpyrylium cation, wherein the pyrylium nucleus is substituted by 3 to 5 alkyl substituents which are identical or different from each other and each preferably contains from 1 to about 10 carbon atoms and three of which are situated in the 2-, 4- and 6- position, and an anion selected which from the group consisting of tetrahalogeno aluminates, tetrahalogeno ferrates and halides which comprises the step of reacting a branched alkane comprising about three carbon atoms more than the sum of carbon atoms contained in the alkyl substituents in 3-, 4- and 5-position of the pyrylium cation of which carbon atoms at least one is a tertiary carbon atom with an acylating agent which is a reactive alkylcarboxylic acid derivative wherein the alkyl preferably contains from 1 to about 10 carbon atoms and an alkyl halide preferably containing from 1 to about 20 carbon atoms in the presence of a Lewis acid catalyst selected from the group consisting of aluminium halides, ferric halides and mixtures thereof.

The alkyl substituents in the polyalkyl pyrylium cation may be straight or branched.

The resulting pyrylium salt can further be treated with an inorganic or organic acid whereby the anion is replaced by an anion derived from the inorganic or organic acid.

The above defined process is particularly suited for preparing a pyrylium salt of the formula

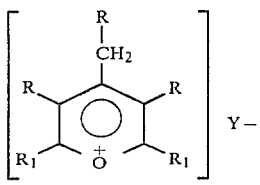

wherein each of the substituents R, which can be identical or different, represent hydrogen or a straight or branched alkyl containing from 1 to about 10 carbon atoms, $R_1$ represents alkyl containing from 1 to about 10 carbon atoms and $Y^-$ represents an anion selected from the group consisting of tetrahalogeno-aluminates, tetrahalogeno ferrate and halides by reacting a branched alkane of the formula

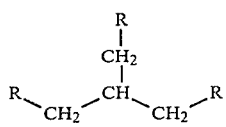

wherein R is as defined above with an acylating agent of the formula $$R_1-CO-Z \qquad (III)$$

wherein $R_1$ is as defined above and Z represents halogen or a group of the formula:

$$R_1-CO-O \qquad (IV)$$

wherein $R_1$ is as defined above, and with an alkyl halide of the formula:

$$R_2-X \qquad (V)$$

wherein $R_2$ represents a straight or branched alkyl group containing from 1 to about 20 carbon atoms, which is unsubstituted or substituted by at least one halogen, with the restriction that only one halogen is bound to the same carbon atom, and X represents halogen, in the presence of the Lewis acid catalyst.

The resulting pyrylium salts of formula I can be treated with any desirable inorganic or organic acid whereby an anion exchange takes place and a compound of formula Ia is formed

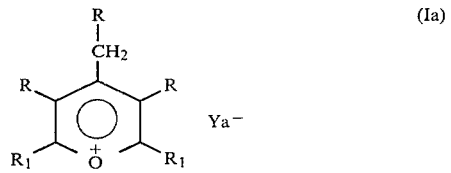

wherein R and $R_1$ are as defined above; $Ya^-$ represents an anion derived from the inorganic or organic acid.

Other objects, features and advantages of the present invention will become apparent to those skilled in the art from the detailed description which follows.

DETAILED DESCRIPTION OF THE INVENTION

The alkyl substitutents in the polyalkylpyrylium salts which are prepared according to the present invention are linear or branched alkyl groups. Examples of suitable alkyl substituents in formulae I and Ia are methyl, ethyl, n-propyl, n-hexyl, n-heptyl, n-decyl, isopropyl and 2,2-dimethylpropyl; $R_1$ can be methyl, ethyl, isopropyl, n-butyl, sec.-butyl, t-butyl, pentyl, hexyl or decyl.

$Y^-$ in the salts of formula Ia represents an anion derived from an inorganic or organic acid. The following anions may be cited as examples of inorganic anions, without implying a limitation: chloride, bromide, iodide, sulphate, nitrate, perchlorate and trifluoroborate ions, tetrafluoroaluminate, tetrachloro- and tetrabromoaluminate and tetrachloroferrate ions, and halogenozincate, -titanate, -antimonate and -stannate ions; examples of suitable anions derived from organic acids are, in particular, sulphonates such as benzenesulphonate, toluenesulphonate, ethanesulphonate and trifluoromethanesulphonate.

Suitable acylating agents of formula (III) are halides such as acetyl chloride, acetyl bromide, propionyl chloride, n-butyryl chloride, n-pentanoyl chloride, isobutyryl chloride, isovaleryl bromide or pivaloyl chloride; it is also possible to use alkylcarboxylic acid anhydrides such as acetic acid anhydride, propionic acid anhydride or butyric acid anhydride. However, acid halides are the preferred acylating agents.

The alkyl halide used in the process according to the invention can contain one or more halogens, with the restriction that, in the latter case, no more than one halogen atom is carried by the same carbon atom. They can be represented by the general formula:

$$R_2-X \qquad (V)$$

in which $R_2$ represents a linear or branched alkyl radical containing from 1 to about 20 carbon atoms, which is optionally substituted by one or more halogen atoms, with the above mentioned restriction; X represents a halogen, namely iodine, fluorine, chlorine or bromine; X is preferably chlorine or bromine.

The following are examples of suitable alkyl halides which can be employed in the process of the present invention: methyl chloride, methyl bromide, ethyl chloride, ethyl bromide, 1,2-dichloroethane, n-propyl chloride, isopropyl chloride and-bromide, and n-butyl-, isobutyl-, t-butyl-, sec.-butyl-, n-pentyl-, t-amyl-, 3methylbutyl-, 2,3-dimethylbutyl-, n-hexyl-, n-octyl-, 2-ethylhexyl- and n-decyl chlorides and-bromides. Alkyl monochlorides and-monobromides having from 1 to about 10 carbon atoms are preferably used.

Non-limiting examples of branched alkanes of the formula (II) which can be used to prepare the pyrylium salts are: isobutane, isopentane, 2-methylpentane, 3-methylpentane, 2-methylhexane, isooctane 2,2,4-trimethylpentane and 2,3-dimethylbutane.

Among the branched alkanes mentioned above, isoalkanes are preferably used, that is to say alkanes of the formula (II) in which the two substitutents R, located on the carbon atoms in the 1- and 3-position in the formula (II), represent identical alkyls and the alkyl situated in the 2-position is a linear or branched alkyl group. Isoalkanes containing from about 4 to about 10 carbon atoms are very particularly suitable.

Without in any way limiting the scope of the invention to a particular mechanism, the reaction can be represented, in the case where the acylating agent is an alkanoyl halide, by the following equation:

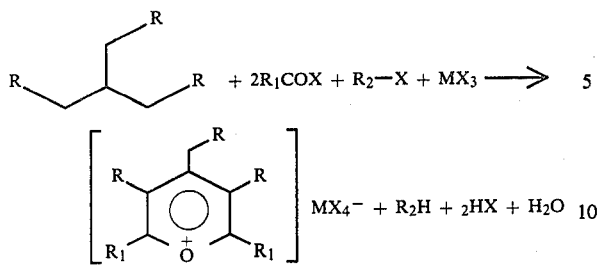

It is found that during the reaction, the alkyl halide is reduced into the corresponding alkane which can be used to prepare the starting alkyl halide by means of conventional processes. It has been observed that, surprisingly, when the alkyl halide is a tertiary halide, such as t-butyl chloride or isoamyl chloride, diacylation of the latter which is described in the literature is virtually non-existent in the presence of the branched alkane.

It has also been found that, in the case where at least two of the substituents are different, the reaction leads to the formation of a mixture of pyrylium salts. Thus, starting from a branched alkane of the formula:

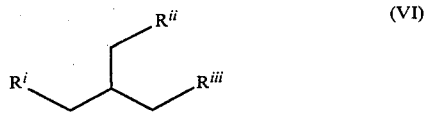

in which the substituents R', R" and R''' are different, it is possible to obtain the following compounds

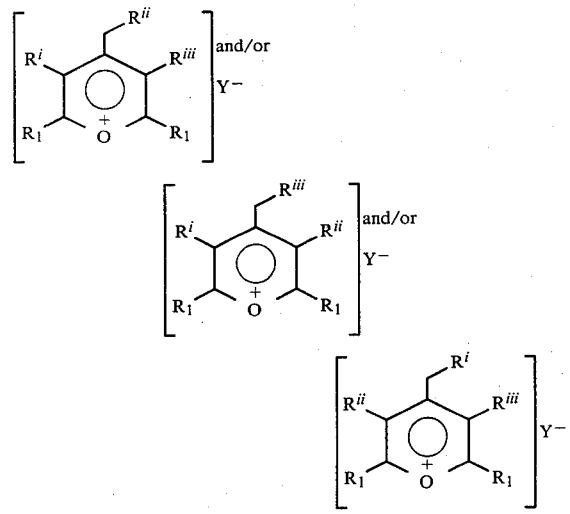

When the reaction is carried out starting from isoalkanes of the general formula:

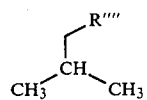

the reaction leads to the formation of the isomeric pyrylium salts:

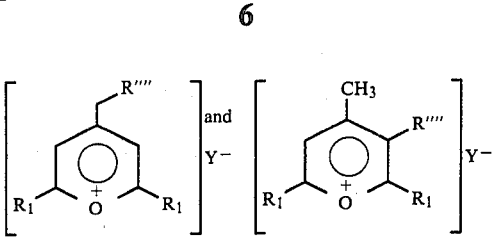

For a given branched alkane, the respective amounts of isomeric pyrylium salts formed depend on the reaction conditions, for example on the amount of Lewis acid, the acylating agent and the temperature, so that it is possible to influence the formation of the isomeric salts by judiciously selecting these various factors.

The respective amounts of branched alkane and acylating agent can vary within wide limits and it is generally possible to use an excess of one or the other of these reactants, relative to the molar proportions which are theoretically required. Thus, it is possible to employ from about 0.1 to about 10 moles of alkane per mole of acylating agent. However, it is preferable to carry out the reaction in the presence of an amount of alkane which is at least equal to that which is theoretically required for carrying out the diacylation. Thus, at least about 0.5 moles of alkane per mole of acylating agent, and in particular from about 0.5 to about 2 moles of alkane per mole of acylating agent are preferably employed.

The amount of alkyl halide employed depends on its nature. Thus, if the alkyl halide is any primary halide, it is possible to use a large excess relative to the amount which is theroretically required; thus, there is no critical upper limit and the maximum amount is determined by practical considerations. In general, the amount of alkyl halide can be between about 0.1 and about 10 moles per mole of alkane. On the other hand, if the alkyl halide is itself capable of undergoing diacylation under the reaction conditions, to lead to pyrylium salts (this being the case of tertialry alkyl halides and secondary alkyl halides), it is preferable not to use too large an excess of alkyl halide, relative to the amount of branched alkane. Thus, the amount of alkyl halide used is in the range of the stoichiometric amount, that is to say approximately one mole of alkyl halide per mole of branched alkane. In this case, the amount of tertiary or secondary halide is preferably between about 0.9 and about 1.1 moles per mole of alkane.

Regardless of whether the aluminium halides or iron halides are used alone or in a mixture with one another, the overall amount of catalyst, expressed as the number of moles of Lewis acid per mole of acylating agent, depends on the nature of the latter. As a general rule, the amount of catalyst employed is in the range of the stoichiometric amount of the acylating agent/catalyst system in question; it is possible to use an excess of catalyst, relative to the stoichiometric amount, but this does not represent a particular advantage. There is also no advantage in employing too small an amount of Lewis acid, relative to the amount which is theoretically necessary for the system in question. In general, a total amount of Lewis acid of between about 0.2 and about 2.5 moles per mole of acylating agent is very suitable; this amount is preferably between about 0.4 and about 1.5 moles per mole of acylating agent.

When using a mixture of an aluminium halide and a ferric halide for carrying out the process according to the present invention, the respective amounts of the constituents of the mixture can vary within wide limits. These proportions are determined according to the influence exerted by each of the constituents on the selectivity of the reaction with respect to the various pyrylium salts. This influence can be determined in each case by means of simple experiments. In general, when using a mixture of an aluminum halide and a ferric halide, the molar proportions of each of these in the mixture can vary between about 0.1 and about 99.9%.

The temperature at which the reaction is carried out can vary between about 0° and about 100° C. and preferably between about 15° and about 80° C. It is not generally necessary to exceed a temperature of 50° C. The reaction is preferably carried out at a temperature between about 15° and about 30° C. Although it is not generally necessary to operate under pressure, it can be advantageous to carry out the reaction under autogenous pressure when one of the reactants is a gas under the reaction conditions.

The process according to the invention can be carried out in the absence of any solvent or in the presence of an organic solvent which is inert under the reaction conditions. Examples of suitable such solvents are carbon disulphide, carbon tetrachloride, chloroform, nitrobenzene, nitrotoluene, nitromethane, nitroethane and nitropropane. The presence of small amounts of water in the reaction medium is not disadvantageous and it is not necessary to use anhydrous reactants. In particular, the catalysts which can be used are metal halides which need not undergo a suitable treatment for rendering them anhydrous.

From a practical point of view, various methods can be used for carrying out the process according to the invention. For example, it is possible to gradually introduce the alkyl halide and the acylating agent, successively or simultaneously, into the alkane containing the catalyst, whereby the temperature of the reaction medium is maintained at the chosen value. The alkyl halide is preferably added to a mixture comprising the alkane, the catalyst, the acylating agent and, optionally, an inert solvent. In this case, this mixture is advantageously kept at as low a temperature as possible during the addition of the alkyl halide. This addition temperature is advantageously between $-10°$ and 0° C. When the introduction of the alkyl halide is completed, the temperature is brought to the value chosen for the reaction if appropriate. The duration of the addition of the alkyl halide can vary. However, this addition is preferably carried out in as short a period of time as possible. Thus, the duration of the addition is preferably less than 10 minutes and more particularly less than 5 minutes. If one of the reactants is a gas under the reaction conditions (branched alkane or alkyl halide), it is possible to carry out the reaction in an autoclave or to gradually feed the gaseous reactant or reactants into a solution or suspension of the catalyst in an inert solvent, which is maintained at the appropriate temperature.

The pyrylium salts obtained by the process according to the invention can be separated from the reaction medium by known methods, for example by extraction with water. Thus, aqueous solutions of pyrylium salts are obtained in which the anion is the conjugate base of the Lewis acid. In order to obtain pyrylium salts derived from other acids, it suffices to treat the reaction mixture, or the aqueous solution resulting from extraction, with the desired acid such as perchloric, sulphuric, hydrochloric or sulphonic acid. If it is desired to use the pyrylium salts as intermediates in organic synthesis, for example in the preparation of substituted phenols and pyridines, it is not necessary to isolate them; thus, the reaction mixture resulting from the diacylation of branched alkanes can be treated with an alkali metal base to yield phenols, or with ammonia or amines to yield heterocyclic bases, in accordance with known processes.

The process according to the invention is of very particular industrial value, because it makes it possible to use mixtures of branched and unbranched alkanes, and, in particular, cuts of paraffins having from 5 to 8 carbon atoms as the starting material in the synthesis of pyrylium salts and, if desired, in the synthesis of substitute phenols and pyridines.

The following examples illustrate the invention and show how it can be put into practice. In these examples, the pyrylium salts were identified and determined in the form of the corresponding pyridines obtained by treating the reaction mixture resulting from diacylation with ammonia.

EXAMPLE 1

26.7 g (0.2 mole) of aluminium chloride were introduced into a 400 cm$^3$ cylindrical glass reactor which is cooled by an ice bath and equipped with a stirrer of the vibro-mixer type, a reflux condenser cooled by circulating alcohol kept at $-15°$ C., a dropping funnel and a thermometer; 36 g (0.5 mole) of isopentane were then introduced, while keeping the temperature in the apparatus at 0° C. 7.85 g (0.1 mole) of isopropyl chloride and then 23.55 g (0.3 mole) of acetyl chloride were then added dropwise. The temperature of the reaction mixture was then allowed to rise to 27° C. and the mixture was stirred for 2 hours 30 minutes under these conditions. After this period liberation of hydrochloric acid had finished.

The resulting reaction mixture was cooled to 0° C. and 250 cm$^3$ of an aqueous ammonia solution of 36% strength by weight were then introduced into the apparatus. The formed organic products were extracted by treating the reaction mixture continuously with chloroform in a liquid-liquid extractor. The chloroform solution was then treated with an aqueous 10% hydrochloric acid solution and the aqueous phase, containing the pyridine derivatives in the form of their hydrochlorides, was then separated from the chloroform phase. The aqueous phase was neutralized with sodium hydroxide and the pyridines were extracted by treating the aqueous phase continuously with dichloromethane in a liquid-liquid extractor.

Dichloromethane was then evaporated from the obtained organic phase and 9.35 g of an organic residue were collected in this way and subjected to analysis. The components thereof were separated by means of preparative vapour-phase chromatography, and subsequently by identification by means of nuclear magnetic resonance and mass spectrometry.

In this manner, in the obtained residue the following compounds were identified and their amount determined:

| | COMPOUND | AMOUNT % BY WEIGHT |
|---|---|---|
| (a) | 4-ethyl-2,6-dimethylpyridine (C₂H₅ at 4-position; CH₃ at 2,6) | 35.3 |
| (b) | 3,4,2,6-tetramethylpyridine (CH₃ at 3,4; CH₃ at 2,6) | 41.4 |
| (c) | 4,2,6-trimethylpyridine | 1.4 |
| (d) | 4-isopropyl-2,6-dimethylpyridine (CH₃,CH₃ isopropyl at 4; CH₃ at 2,6) | 1.7 |
| (e) | 4-methyl-3-ethyl-2,6-dimethylpyridine | 1.1 |
| (f) | 4-(1-acetyl-1-methyl)-2,6-dimethylpyridine (CH₃—CO, CH₃ at 4; CH₃ at 2,6) | 2.5 |
| (g) | 4-acetyl-3,2,6-trimethylpyridine (CO-CH₃ at 4; CH₃ at 3,2,6) | 16.4 |

COMPARISON EXPERIMENT 1

For comparison, the procedure described in Example 1 was repeated, but the reaction was carried out in the absence of isopropyl chloride. Under these conditions, it was found that hydrochloric acid was liberated only when the temperature reached 35° C. A reaction time of 5 hours 30 minutes was necessary, whereby the temperature was allowed to rise to 45° C., before it was observed that the liberation of hydrochloric acid had stopped.

After treating the reaction mixture as in Example 1, 7.45 g of a mixture of pyridines were obtained, in which the following compounds were identified and determined:

| Compounds | Percentage by weight |
|---|---|
| (a) | 17.6 |
| (b) | 67.9 |
| (c) | 1.6 |
| (f) | 6.5 |
| (g) | 6.4 |

COMPARISON EXPERIMENT 2

The procedure of Example 1 was repeated, but the isopentane is replaced by t-amyl chloride and the reaction was carried out in the absence of isopropyl chloride. The reaction was finished after 3 hours 30 minutes at 30°–35° C.

After treating the reaction mixture as in Example 1, 3.9 g of a mixture of pyridines were obtained, in which the following compounds were determined and identified:

| Compounds | Percentage by weight |
|---|---|
| (a) | 20.2 |
| (b) | 24.3 |
| (c) | 14.1 |
| (d) | 2.4 |
| (e) | 2.1 |
| (f) | 5.8 |
| (g) | 19.2 |
| (h) 4-(1-acetyl-1-ethyl)-2,6-dimethylpyridine (CH₃CO, C₂H₅ at 4; CH₃ at 2,6) | 2.9 |
| (i) 4-(acetylmethyl)-3-ethyl-2,6-dimethylpyridine (COCH₃, C₂H₅; CH₃ at 2,6) | 1.2 |

The proton nuclear magnetic resonance spectra (PNMR) of compounds (d) to (i) show the following characteristics:

Compound (d) in carbon tetrachloride: doublet at 1.22 ppm; singlet at 2.42 ppm; hump at 2.7 ppm; singlet at 6.67 ppm.

Compound (e) in deuterated chloroform: triplet at 1.1 ppm; singlet at 2.23 ppm; singlets at 2.5, 2.6 and 6.76 ppm.

Compound (f) in deuterated chloroform (CDCl₃): doublet at 1.48 ppm; singlets at 2.08, 2.52 and 6.84 ppm; quadruplet at 3.66 ppm.

Compound (g) in CDCl₃: singlets at 2.12, 2.17, 2.45, 2.49, 3.68 and 6.76 ppm.

Compound (h) in CDCl₃: triplet at 0.83 ppm; singlets at 2.15, 2.46 and 6.82 ppm.

Compound (i) in CDCl₃: triplet at 1.08 ppm; singlets at 2.16, 2.48, 3.64 and 6.77 ppm; masked quadruplet at 2.56 ppm.

In the following examples, (a), (b), (c), (d), (e), (f), (g), (h), and (i) will denote the pyridine compounds, the same formulae which are given in the present example.

EXAMPLE 2

The procedure of Example 1 was followed, but the aluminium chloride was replaced by 32.5 g of ferric chloride and the isopropyl chloride was replaced by 9.25 g of t-butyl chloride.

Under these conditions, after treating the reaction mixture as in Example 1, 9.3 g of a mixture of pyridines was obtained, in which the following compounds were determined and identified:

(a) 60.8% by weight
(b) 17.4%
(c) 4.1%
(f) 0.8%

(g) 16.7%

EXAMPLE 3

The procedure of Example 1 was followed, but the isopentane was replaced by 43 g (0.5 mole) of 3-methylpentane and the acetyl chloride and subsequently the isopropyl chloride were added successively when the temperature reached 15° C. The reaction mixture was kept at 28° C. for 3 hours 30 minutes. After treating the reaction mixture as in Example 1, 7.6 g of a mixture of pyridines were collected, in which the following compounds were identified and determined:

| | | |
|---|---|---|
| (j) | [structure: 4-C$_2$H$_5$-2,3,6-trimethylpyridine] | 13.3 % by weight |
| (k) | [structure: 2,3,4,4,6-pentamethyl... 4-CH$_3$ on trimethylpyridine] | 34.9 % by weight |
| (c) | | 0.7 % by weight |
| (a) | | 0.4 % by weight |
| (d) | | 1.2 % by weight |
| (e) | | 31.1 % by weight |
| (l) | [structure: 4-C$_3$H$_7$-2,6-dimethylpyridine] | 11.8 % by weight |
| (h) | | 1.1 % by weight |
| (m) | [structure: CH$_3$CO-CH(CH$_3$)- on 2,3,6-trimethylpyridine] | 2.4 % by weight |
| (i) | | 1.9 % by weight |
| (n) | [structure: -CH$_2$COCH$_3$ on 2,3,5,6-tetramethylpyridine] | 0.9 % by weight |

COMPARISON EXPERIMENT

The procedure of Example 2 was repeated by way of comparison, but the reaction was carried out in the absence of isopropyl chloride. The amounts of reactants were as follows:

| | |
|---|---|
| 3-methylpentane | 86 g |
| acetyl Chloride | 40 g |
| aluminium chloride | 46.7 g |

The reaction time was 4 hours at 44° C.

After treating the reaction mixture, 8.8 g of a mixture of pyridines were collected, in which the following compounds were determined and identified:

| | |
|---|---|
| (c) | 0.5% by weight |
| (d) | 0.3% by weight |
| (e) | 43.5% by weight |

-continued

| | |
|---|---|
| (l) | 8.2% by weight |
| (h) | 6.6% by weight |
| (m) | 6.2% by weight |
| (i) | 10.7% by weight |
| (n) | 3.2% by weight |
| (j) | 7% by weight |
| (k) | 12.8% by weight |

The proton nuclear magnetic resonance spectra of the compounds (j) to (h) show the following characteristics:

Compound (j) in CDCl$_3$: triplet at 1.16 ppm; singlet at 2.16, 2.48 and 6.67 ppm; quadruplet at 2.56 ppm.

Compound (k) in CDCl$_3$: singlets at 2.2 and 2.5 ppm.

Compound (l) in CDCl$_3$: triplet at 0.89 ppm; hump at 1.57 ppm; singlet and triplet at 2.45 ppm; singlet at 6.74 ppm.

Compound (m) in CDCl$_3$: doublet at 1.31 ppm; singlets at 2, 2.2, 2.43, 2.46 and 6.7 ppm; quadruplet at 3.9 ppm.

Compound (n) in CDCl$_3$: singlets at 2.14, 2.22, 2.5 and 3.82 ppm.

EXAMPLE 4

The procedure of Example 3 was followed, but 3-methylpentane was replaced by 2-methylpentane. The reaction time was 2 hours 30 minutes at 30° C.

6.7 g of a mixture of pyridines were collected, in which the following compounds were determined:

| | |
|---|---|
| (d) | 0.5% by weight |
| (e) | 32% by weight |
| (j) | 7% by weight |
| (k) | 18% by weight |
| (l) | 17% by weight |
| (h) | 5% by weight |
| (m) | 7% by weight |
| (i) | 10% by weight |
| (n) | 6% by weight |

EXAMPLE 5

The procedure of Example 4 was followed, but 2-methylpentane was replaced by 2,3-dimethylbutane. 5.6 g of a mixture of pyridines were collected, in which the following compounds were determined and identified:

| | | |
|---|---|---|
| (c) | | 0.8% by weight |
| (d) | | 37.6% by weight |
| (e) | | 1.3% by weight |
| (j) | | 2.1% by weight |
| (k) | | 1.1% by weight |
| (l) | | 0.9% by weight |
| (m) | | 1.3% by weight |
| (i) | | 1.4% by weight |
| (o) | [structure: 4-C(CH$_3$)$_2$COCH$_3$-2,6-dimethylpyridine] | 37% by weight |

Compound (o) possesses a PNMR spectrum having the following characteristics: singlets at 1.43, 1.92, 2.5 and 6.83 ppm.

EXAMPLE 6

53.4 g (0.4 mole) of aluminium chloride was introduced into a glass reactor such as that described in Example 1.

14.4 g (0.2 mole) of isopentane in 50 g of chloroform and then 31.4 g (0.4 mole) of acetyl chloride were added, while keeping the temperature at 0° C. The temperature was brought to 30° C. and 15.7 g (0.2 mole) of isopropyl chloride in 50 g of chloroform were then added dropwise. Hydrochloric acid was liberated rapidly and the liberation stopped after 3 hours under these conditions. The reaction mixture was kept at 30° C. for a further 12 hours. The reaction medium was a clear deep yellow liquid. About 200 cm$^3$ of ammonia solution (d=0.92) were then poured in, whereby precautions were taken at the start because the reaction was very vigorous (the mixture was cooled by means of an ice bath). An organic phase and an aqueous phase containing the dense precipitate of the aluminium salts were thus obtained. This mixture was poured into an approx. 800 cm$^3$ liquid-liquid extractor. The reactor was washed with about 200 cm$^3$ of ammonia solution and chloroform and the washing liquid was added to the contents of the extractor. The organic products resulting from the reaction were extracted continuously with about 300 cm$^3$ of chloroform (the duration of the extraction was 6 hours). Afer evaporating the chloroform, the mixture of organic compounds were treated with about 150 cm$^3$ of 10% hydrochloric acid (up to pH=1). The aqueous and organic phases were separated. The aqueous phase was washed with about 20 cm$^3$ of chloroform. The aqueous phase was brought to pH=12 by adding sodium hydroxide pellets. The resulting free pyridines were extracted continuously from the aqueous phase with about 150 cm$^3$ of methylene chloride in a 300 cm$^3$ extractor. The methylene chloride was then evaporated and a residue weighing 10.7 g was obtained, in which the following compounds were identified and determined:

| | |
|---|---|
| (a) | 0.96% by weight |
| (b) | 94% by weight |
| (c) | 1.4% by weight |
| (g) | 0.6% by weight |

EXAMPLE 7

200 g of freshly distilled anhydrous chloroform and then 0.2 moles (26.7 g) of aluminium chloride were placed into a cylindrical glass reactor equipped with a double jacket, a stirrer of the vibro-mixer type and a reflux condenser. Water at 0° C. was circulated in the double jacket and alcohol at −40° C. was circulated in the reflux condenser. Then stirring was started. 0.2 moles of acetyl chloride and then 0.1 moles (8.6 g) of 2-methylpentane were added. Still at 0° C., 0.1 moles (7.85 g) of isopropyl chloride are added using a piston-type burette so that the addition took place within 2 minutes, the temperature of the reaction medium was then brought to 25° C. and the reaction was allowed to proceed for 2 hours.

The reaction medium was cooled (circulation of water at 0° C.) and then poured into a glass conical flask containing 500 ml of an aqueous 34% ammonia solution and about 100 g of ice, while maintaining efficient stirring. The products of the reaction were extracted continuously with chloroform. The pyridines were separated from the mixture by treatment with 5% hydrochloric acid. The aqueous phase containing the pyridinium salts were treated with an excess of sodium hydroxide pellets and the pyridines were then extracted continuously with methylene chloride.

After evaporating the solvent, the mixture of pyridines was dried in a desillator over sodium hydroxide and then weighed and analyzed by gas phase chromatography.

The chloroform phase containing these reaction products which were not pyridines were evaporated off and this residue was dried over calcium chloride in a desiccator and then weighed.

4.1 of residue of non-pyridines and 5.1 g of a mixture of pyridines, which were identified and determined as in Example 1, were collected in this way. The following compounds were identified:

| | |
|---|---|
| (e) | 86.5% |
| (l) | 4.4% |
| (j) | 1.6% |

2,6-dimethylpyridine 3.5%.

It was found that the products resulting directly from the diacylation of 2-methylpentane ((e) and (1)) constituted 90.9% of the pyridine products.

What is claimed is:

1. A process for preparing polyalkylpyrylium salts comprising a polyalkylpyrylium cation, wherein the pyrylium nucleus is substituted by 3 to 5 alkyl substituents which are identical or different from each other and three of which are situated in the 2-, 4- and 6-position, and an anion selected from the group consisting of tetrhalogeno-aluminates, tetrahalogenoferrates and halides which comprises the step of reacting a branched alkane comprising about three carbon atoms more than are contained in the alkyl substituents in 3-, 4- and 5-position of the pyrylium cation of which atoms at least one is a tertiary carbon atom with an acylating agent which is a reactive alkyl carboxylic acid derivative suitable for use as an acylating agent and an alkyl halide in the presence of a catalytically effective amount of a Lewis acid catalyst selected from the group consisting of aluminium halides, ferric halides, and mixtures therof, said branched alkane, acylating agent, and alkyl halide being reacted in an amount sufficient and at a temperature and for a length of time sufficient to form said polyalkylpyrylium salts.

2. The process as defined in claim 1 wherein the alkyl substituents in the polyalkylpyrylium cation each contain from 1 to about 10 carbon atoms and wherein the alkyl in the alkyl carboxylic acid derivative contains from 1 to about 10 carbon atoms and the alkyl halide contains from 1 to about 20 carbon atoms.

3. The process as defined in claim 1 which further comprises the step of treating the pyrylium salt with an inorganic or organic acid whereby the anion is replaced by an anion derived from the inorganic or organic acid.

4. The process as defined in claim 1, for preparing a pyrylium salt of the formula

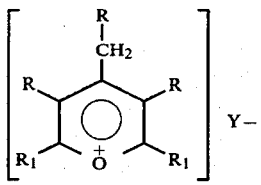 (I)

wherein each of the substituents R, which can be identical or different, represent hydrogen or alkyl containing from 1 to about 10 carbon atoms, $R_1$ represents alkyl containing from 1 to about 10 carbon atoms and $Y^-$ represents an anion selected from the group consisting of tetrahalogeno-aluminates, tetrahalogeno-ferrates and halides which comprises the step of reacting a branched alkane of the formula

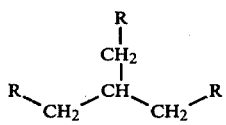 (II)

wherein R is as defined above, with an acylating agent of the formula

 (III)

wherein $R_1$ is as defined above and Z represents halogen or a group of the formula:

 (IV)

wherein $R_1$ is as defined above, and with an alkyl halide of the formula:

 (V)

wherein $R_2$ represents an alkyl group containing from 1 to about 20 carbon atoms, which is unsubsituted or substituted by at least one halogen, with the restriction that only one halogen is bonded to the same carbon atom, and X represents halogen, in the presence of the Lewis acid catalyst.

5. The process as defined in claim 4, wherein in the branched alkane of the formula (II) substituents R located in the 1- and 3-position are identical.

6. The process as defined in claim 4, wherein the branched alkane is seleced from the group consisting of isopentane, 2-methylpentane, 3-methylpentane and 2,3-dimethylbutane.

7. The process as defined in claim 1, wherein the acylating agent is selected from the group consisting of halides and anhydrides of the alkyl carboxylic acids.

8. The process as defined in claim 7, wherein the acylating agent is an alkanoyl chloride or an alkanoyl bromide.

9. The process as defined in claim 8, wherein the acylating agent is acetyl chloride.

10. The process as defined in claim 1, wherein the alkyl halide is an alkyl chloride or an alkyl bromide.

11. The process as defined in claim 10, wherein the alkyl halide is isopropyl or t-butyl chloride.

12. The process as defined in claim 1, wherein the Lewis acid catalyst is selected from the group consisting of aluminium chloride, ferric chloride and mixtures thereof.

13. The process as defined in claim 1, wherein the reaction is carried out in an inert organic solvent.

14. The process as defined in claim 12, wherein the organic solvent is chloroform.

15. The process as defined in claim 1, wherein the branched alkane is employed in an amount of between about 0.1 and about 10 moles per mole of the acrylating agent.

16. The process as defined in claim 1, wherein the alkyl halide is employed in an amount of at least about 0.1 mole per mole of branched alkane.

17. The process as defined in claim 1, wherein the Lewis acid catalyst is employed in an amount of between about 0.2 and about 2.5 moles per mole of acylating agent.

18. The process as defined in claim 1, wherein the reaction is carried out at a reaction temperature of between about 0° and about 100° C.

19. The process as defined in claim 4, wherein the anion $Y^-$ is tetrachloroaluminate and tetrachloroferrate.

* * * * *